Figure 1:
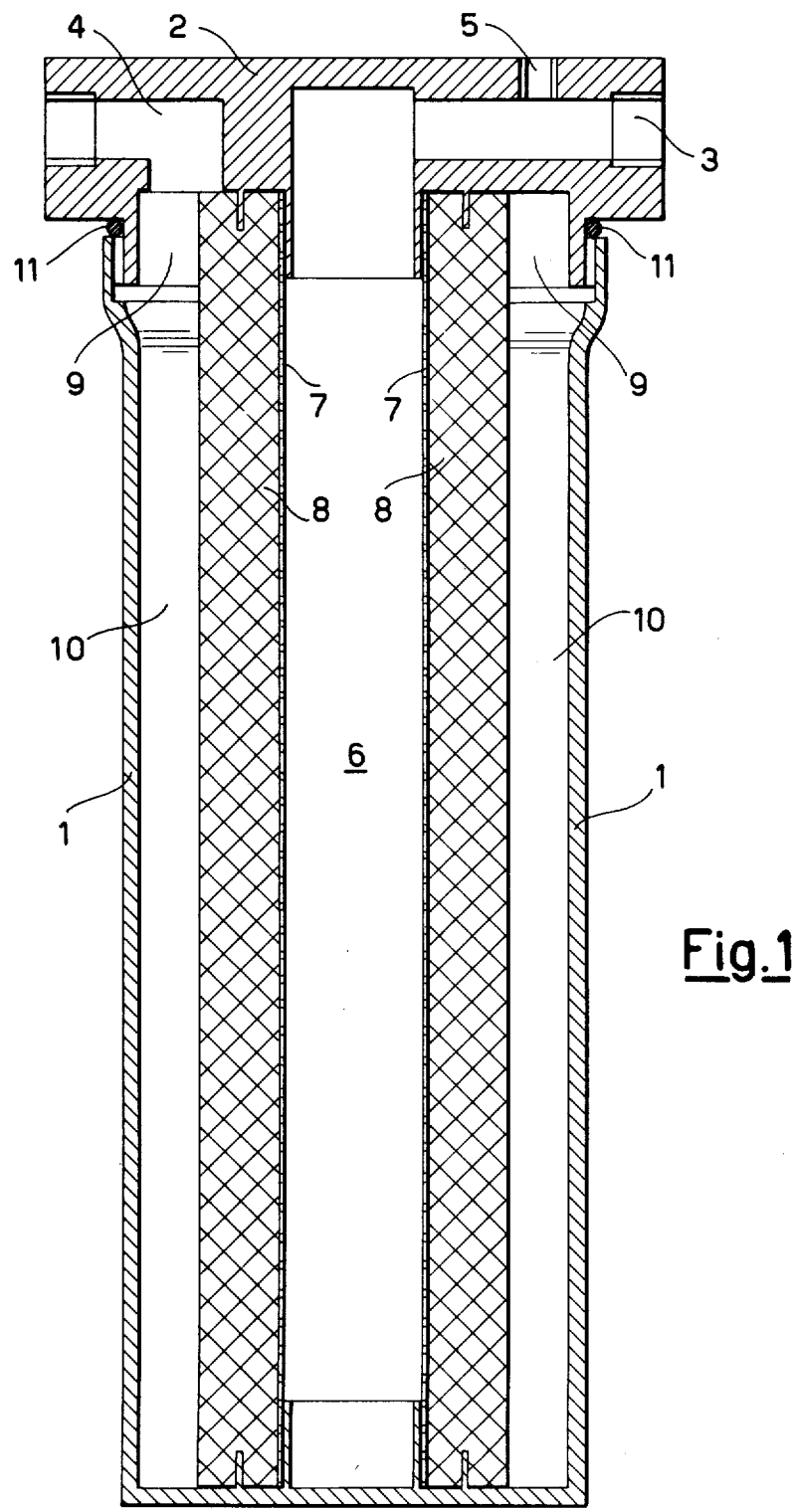

United States Patent [19]

Bartoli et al.

[11] 4,242,461
[45] Dec. 30, 1980

[54] RADIAL REACTOR FOR ENZYME-CATALYZED REACTIONS

[75] Inventors: Francesco Bartoli; Franco Morisi, both of Rome; Delio Zaccardelli, Monterotondo, all of Italy

[73] Assignee: Snamprogetti S.p.A., Milan, Italy

[21] Appl. No.: 941,682

[22] Filed: Sep. 12, 1978

[30] Foreign Application Priority Data

Oct. 13, 1977 [IT] Italy ............................ 28553 A/77

[51] Int. Cl.³ .................................................. C12M 1/40
[52] U.S. Cl. ...................................... 435/288; 422/218
[58] Field of Search ................. 435/288, 287; 422/218

[56] References Cited

U.S. PATENT DOCUMENTS

| | | | |
|---|---|---|---|
| 2,635,989 | 4/1953 | Bonner | 422/218 X |
| 2,639,224 | 5/1953 | McAfee | 422/218 |
| 2,997,374 | 8/1961 | Lavender, Jr. et al. | 422/218 |
| 3,362,792 | 1/1968 | Ranum | 422/218 X |
| 3,769,175 | 10/1973 | Berdelle-Hilge | 435/288 |
| 3,775,063 | 11/1973 | Grout et al. | 435/288 |
| 3,809,613 | 5/1974 | Vieth et al. | 435/288 |
| 3,917,811 | 11/1975 | Grout et al. | 435/288 |

*Primary Examiner*—Robert J. Warden
*Attorney, Agent, or Firm*—Morgan, Finnegan, Pine, Foley & Lee

[57] ABSTRACT

For effecting enzymic reaction, a reactor is disclosed, in which the flow of the solution to be treated through the catalytic bed material takes place radially. It is preferred to have the catalytic bed in the form of coils of enzyme-occluding fibers. The coils are variously piled up within the reactor. High outputs, low pressure drops and more than satisfactory conversion rates are obtained.

9 Claims, 1 Drawing Figure

RADIAL REACTOR FOR ENZYME-CATALYZED REACTIONS

This invention relates to a radial reactor for performing enzyme-catalyzed reactions.

More particularly, the present invention relates to a radial reactor for enzymic catalysis, having fixed catalytic beds having a cylindrical symmetrical outline and through which the solutions to be treated are caused to flow in a radial direction.

Enzyme-catalyzed reactions effected in heterogeneous liquid-solid systems with catalysts for a proteinic type which are immobilized on an insoluble substrate by covalent or ionic bonds, by adsorption or occlusion, require that the following conditions may concurrently be fulfilled:

(a) a high velocity of flow of the solution which contains the enzyme-substrates dissolved therein to reduce the diffusion resistances external to the catalyst-substrate, which limit the transfer phenomena from the movable phase to the fixed phase;

(b) low pressure drops for reducing the initial and running costs relative to the flow of the liquor and also to prevent detrimental collapses of the catalytic bed.

It is to be considered, moreover, that many of the systems which immobilize enzymes have poor mechanical properties and undergo both elastic and non-elastic deformations and that the solutions being treated have, in many a case, a high viscosity.

With enzymic catalysts occluded in fibers according to the Italian Pat. Specification No. 836,462, reactors have been made in which the fibers were arranged parallely to the reactor axis or had the form of a felt after having been severed in pieces of the length of a few centimeters.

These axial-flow cylindrical reactors have already enabled satisfactory results to be achieved under the respects of the efficiency of the catalytic bed and the pressure drops.

It has now been surprisingly ascertained, and this is the subject matter of this invention, that it is possible to improve the results mentioned above by adopting radial reactors for catalysis, which are fixed and have a cylindrical symmetry and through which the solutions being treated are radially caused to flow.

The radial reactors according to the present invention are composed by a chamber for distributing the streams, which is cylindrical and formed by a foraminous pipe and is inserted in the interior of a catalytic body having an annular shape, and by a chamber for collecting the treated liquor, the latter chamber being confined by the catalytic bed as such and by the reactor hood.

The solutions to be treated enters the central distribution chamber, flows through the catalyst radially with a direction of flow perpendicular to the fiber axis and, after having reacted, is collected in the outermost collection chamber. It is apparent, from what has been set forth above, that the radial flows can also be caused to circulate in the opposite sense, in which case the central chamber is the collection chamber whereas the peripheral chamber is the distribution chamber.

The catalytic beds are prepared outside the reactor in a controlled and uniform way to prevent the formation of preferential paths and to optimize the conversion efficiencies of the enzyme substrates and the costs for having the solutions to be treated flowing.

The catalytic beds are obtained by winding the fibers, on which the enzymes are supported, so as to form coils with filaments or groups of filaments arranged helically with different pitches consistently with the particular hydraulic and chemical requirements involved: more particularly, the helix pitch can lie between 0.001 mm and 10 cm. The fibers which are used can be monofilamentary, yarns, twisted and obtained from monofilaments, webs or staples.

More detailedly, the coils are obtained by windings made with different angles of the thread relative to the generating line of the wound surface (angle of incidence of the thread) and different tension of the thread on cores of different shapes constructed with any configuration and material and having, or not, sealing fitt-ings or not, by screw-threads, clamping and others.

Very useful have proven to be the coils obtained from cores having a cylindrical, a conical or a frustoconical shape: in the case of cores having a conical or frustoconical shape, they are inserted in the interior of the reactor in such a way as to have arranged alternatingly in side-by-side relationship the cone bases with the cone tips or, in the case of frustoconical cores, the larger bases with the smaller bases.

The winding, moreover, can be made with thin tubes having permeable walls which contain in their interior an enzymic solution.

The cores so obtained are stacked in the interior of the reactor and, in the majority of the cases, are wrapped overall by a sheath which has the task of preventing deformations and the resultant provision of preferential paths or stagnation spots.

The fibers inserted in the reactor the subject of the* present invention can also support, instead of enzymes, chelation agents, antibodies or similar products which are immobilized, like the enzymes, by physical bonds, ion exchange, adsorption or occlusion in filamentary polymeric structures.

Having now references to the accompanying single FIGURE of the drawing, the reactor according to the present invention will be illustrated by way of example without limitation.

The reactor is composed by a body 1, to which is affixed, by bolts not shown, the lid or cover 2. In the interior of the cover channels 3 and 4 are provided, which are used as feed channels for the solution to be treated (channels 3) and as discharge channels for the treated solution (channel 4). To the channel 3 a vent 5 is connected which has the task of discharging the incoming solution from the reactor in the case that the latter is to be stopped for any reason.

In the interior of the reactor, the following members are arranged, viz.: the cylindrical distribution chamber 6, coaxial with the reactor and separated from the catalytic bed by the agency of the foraminous pipe 7, the catalyst 8 arranged annularly around the pipe 7 and fastened to the reactor bottom and its lid by appropriate fittings and, lastly, the collection chamber 10 arranged between the reactor hood and the catalyst. Appropriate sealing members 11 ensure the tight seal of the reactor.

The solution enters, through the channel 3, the distribution chamber 6 and, through the foraminous pipe 7, goes to react in the interior of the catalytic bed 8. After having reacted, the solution is collected in the chamber 10 and is discharged through the channels 4 and 9.

As outlined above, the flow of the solution can take place also in the sense opposite to that described just now, and, if so, the collection chamber and the distribution chamber, as well as the intake and outlet channels have their respective functions reversed.

Among the advantages stemming from the use of such reactors, there can be cited: efficiencies higher than those obtained with the other reactors used heretofore, velocities of circulation of the liquors to be treated lying in ranges which are considerably wider than those afforded by the conventional geometrical arrangements, ease and reproducibility of the preparation of the catalytic beds, practicability of working with cartridge sets in series or in parallel so as to standardize the preparation of production plants, to plan the upkeep and replacement of production elements, to adjust the possible feeds in the intermediate stages (pH adjustments, temperature, composition and others), to adapt the linear velocities of the individual stages to the optimum conversion characteristics by selecting the working plots which are best adapted to achieve a maximum efficient.

As compared with the apparatus used for filtration, the radial reactor displays differentiated characteristics since it is concerned with different methods, does not require wide filtering surfaces but reduced interstitial volumes and attributes different functions both to the fiber bed and to the liquids flowing therethrough. The radial reactors differ from the yarn-dying machines both because attribute different functions to the fibers and the circulating liquors and because are concerned with totally different reactions and, lastly, because reactions and chemical conditions are involved which do not afford any possibility of comparison.

A few examples will not be given in the following in order better to illustrate the invention without however limiting it.

EXAMPLE 1

It is known that the isomerization of glucose to fructose as catalyzed by the glucose-isomerase enzyme can be performed with such an enzyme immobilized in cellulose triacetate fibers as disclosed in Italian Patent Specification No. 836,462.

A sample of fibers corresponding to 160 g of polymer has been introduced in a conventional tubular reactor having a diameter of 20 mm and a height of 2,000 mm.

A 60% (wt/vol) solution of glucose in a buffer has been sent to the thermostatically controlled reactor (60° C.) at a rate of flow of 960 mls an hour. On the solution which exited the reactor the conversion of glucose into fructose has been measured and was found to be 0.42. The fructose output was 242 grams an hour.

The relative pressure drop was 2 kg/cm$^2$.

An equal quantity of fibers has been helically wound about a stainless steel core (diameter 32 mm, height 250 mm) obtained from a foraminous sheet 1-mm thick with perforations of a diameter of 3 mm and the foraminous portion of which was 45% of the total area.

The thickness of the fiber panel as obtained was 21 mm.

The coil has been inserted in a cylindrical container (diameter 100 mm; height 250 mm (see item 8 of the FIGURE) having a screwed lid or cover which, by impressing a light pressure on the coil provides a tight seal of it both on the container's bottom and on the lid. The lid has two bores for the inlet and the outlet of the feeding liquor: either bore is near the container's wall and the other is centrally arranged in registry with the coil core. By so doing the coil has, flowing therethrough radially, a stream of liquid, both when feeding the solution to be treated through the bore near the container wall and drawing liquid from the central bore, the same being true if the direction of flow is reversed.

This reactor, thermostatically kept at 60° C. has been fed with 1,200 mls an hour of the glucose solution described previously, in both the two possible directions of flow.

With both types of flow (outside to inside and inside to outside) the effluent liquor showed a conversion equal to 0.42 (which corresponds to a fructose output of 302 grams an hour): the pressure drop was 0.12 kg/cm$^2$.

EXAMPLE 2

With the method described in Example 1, a fiber of cellulose triacetate has been prepared, which contained a solution of concentrated invertase BDH.

160 grams of fibers have been introduced in a tubular reactor (height 500 mm, diameter 45 mm), thermostatically kept at 25° C. A 60% (wt/vol) solution of sucrose in 0.1 M, pH 4.5 potassium phosphate buffer has been fed into the reactor at a rate of flow of 1 liter an hour. On the effluent liquor a conversion of sucrose into glucose and fructose equal to 0.99 has been measured. The output of glucose and fructose was 625 grams an hour.

The reactor worked under a pressure drop of 0.9 kgs/square centimeter. As for example 1, an equal quantity of the same fiber has been wound on a core with a diameter (inside) of 32 mm and a height of 250 mm. The radial reactor has been fed at 25° C. with the sucrose solution described above and a conversion of 0.99 has been obtained for a rate of flow of 1.2 liters an hour. The output of glucose and fructose was 750 grams on hour. The pressure drop was 0.12 kg/cm$^2$.

EXAMPLE 3

The activity of a cellulose triacetate fiber which contains the glucose-isomerase enzyme occluded therein slowly decreases with the lapse of time. After 75 days of work, the residual activity is but one half of the initial one, and after 118 days, it is one quarter, so that the reactor is regarded as exhausted after 118 days.

Usually, in order to keep the conversion in the eluate constant, the reactor feeding rate of flow is acted upon by reducing it proportionally to the activity drop displayed by the reactor. This fact leads to a decrease in output. To keep constant the output, the following procedure has been adopted: a reactor has been constructed, which was capable of holding 12 coils equal to those described in Example 1, which were serially connected to each other. A single coil has been switched initially and for having a conversion of 42% a rate of flow of 1.2 liter an hour has been adopted. Subsequently, a coil every 9 days has been inserted, until having 12 working coils with an average rate of flow of 9 liters an hour. At this stage, the plant was in steady working conditions and, subsequently, by replacing every 9 days an old coil by a new one, the plant has worked at 42% conversion with rates of flow variable from 9.5 liters an hour to 8.5 liters an hour, the output being thus maintained constant within a ±5% variation limit.

EXAMPLE 4

It has been prepared, according to the teachings of example 1, a cellulose triacetate fiber which occluded the beta-galactooxidase enzyme (from *Aspergillus niger*). 30 grams of such fiber have been introduced in a tubular reactor (300 mm of height and 23 mm of diameter thermostatically kept at 60° C. The reactor has been fed by a 5% solution of lactose as obtained by ultrafiltration of cheese-making whey.

The lactose, in the presence of beta-galactooxidase was hydrolyzed to glucose and galactose. To obtain a 99% and 100% conversion, the column was fed at a rate of flow of 0.100 liters an hour. The production of sugars (glucose+galactose) coming from the hydrolysis of lactose was 5.2 grams an hour. The pressure drop was 0.7 kg/cm$^2$.

An equal quantity of fiber has been wound, according to the procedure set forth in example 1, on a core (diameter 21 mm, height 70 mm). The reactor so obtained has been inserted in a cylindrical container (diameter 65 mm; height 75 mm) of the kind of those already described and has been fed, at 60° C., with the solution of lactose described above.

On the effluent a conversion of from 99% to 100% has been obtained with a rate of flow of 0.120 liter an hour and a pressure drop of 0.24 kg/cm$^2$. The output of glucose and fructose was 6.3 grams an hour.

We claim:

1. A radial reactor for performing enzyme-catalyzed reactions with a solution comprising:
    a cylindrically shaped body for receiving the solution to be treated,
    a catalytic bed within said body which is cylindrical and coaxial therewith and wherein said bed is composed of fibers having enzymes occluded therein for treating the solution, the fibers being helically coiled about a core at a pitch from 0.001 mm to 10 centimeters for effecting the treatment of the solution as it flows therethrough,
    a pair of cylindrical chambers within said body and coaxial therewith, wherein one of said chambers is within said catalytic bed and the other of said chambers is about said catalytic bed, and wherein one of said chambers is adapted to receive and to distribute the solution through said catalytic bed radially of said body and the other of said chambers is adapted to collect the reaction product after the solution has flowed through said catalytic bed radially of said body, and
    a cover fastened to said body having an inlet channel open to said distribution chamber for conveying the solution to be treated thereto, a vent open to said inlet channel adapted to discharge the solution within the said inlet channel when said reactor is stopped, and an outlet channel open to said collection chamber for discharging the reaction product of the treated solution from said reactor.

2. The radial reactor of claim 1, wherein said distribution chamber is within said catalytic bed and said collection chamber is about said catalytic bed.

3. The radial reactor of claim 1, wherein said distribution chamber is about said catalytic bed and said collection chamber is within said catalytic bed.

4. The radial reactor of claim 1, wherein a cylindrical foraminous wall is included within said body which defines and is coaxial with the inner of said two chambers and about which said catalytic bed of said helically pitched fibers are coiled.

5. The radial reactor of claim 1, wherein sealing means are provided between said cover and body to prevent leakage of the solution and reaction product.

6. The radial reactor of claim 1, wherein said catalytic bed is comprised of a plurality of stacked helically pitched coils.

7. The radial reactor of claim 6, wherein each of said stacked coils have a shape selected from the group consisting of cylindrical, conical and frustoconical.

8. The radial reactor of claim 7, wherein each of said stacked coils are conical and are stacked in such a way as to alternately place the cone bases and cone tips in contact with each other.

9. The radial reactor of claim 7, wherein each of said stacked coils have a frustoconical shape and are stacked in such a way as to alternately place the larger base in contact with the smaller base of the adjacent coil.

* * * * *